United States Patent
Kelavkar

(10) Patent No.: US 9,903,878 B2
(45) Date of Patent: Feb. 27, 2018

(54) BIOMARKER FOR HUMAN PROSTATE CANCER

(71) Applicant: Uddhav Kelavkar, Savannah, GA (US)

(72) Inventor: Uddhav Kelavkar, Savannah, GA (US)

(*) Notice: Subject to any disclaimer, the term of this patent is extended or adjusted under 35 U.S.C. 154(b) by 488 days.

(21) Appl. No.: 14/591,788

(22) Filed: Jan. 7, 2015

(65) Prior Publication Data

US 2015/0192597 A1  Jul. 9, 2015

Related U.S. Application Data

(60) Provisional application No. 61/924,595, filed on Jan. 7, 2014.

(51) Int. Cl.
*G01N 33/92* (2006.01)
*G01N 33/574* (2006.01)
*G06F 19/00* (2018.01)

(52) U.S. Cl.
CPC ....... *G01N 33/92* (2013.01); *G01N 33/57434* (2013.01); *G01N 2405/04* (2013.01); *G01N 2560/00* (2013.01); *G06F 19/3431* (2013.01)

(58) Field of Classification Search
None
See application file for complete search history.

(56) References Cited

FOREIGN PATENT DOCUMENTS

WO    WO 2011098509 A1 *  8/2011  ........... G01N 33/574

OTHER PUBLICATIONS

Han et al., "Microfluidics-based electrospray ionization enhances the intrasource separation of lipid classes and extends identification of individual molecular species through multi-dimensional mass spectrometry: development of an automated high-throughput platform for shotgun lipidomics," Rapid Commun. Mass Spectrom. 2008, 22:2115-2124.*
Welti et al., "Profiling Membrane Lipids in Plant Stress Responses," J. Biol. Chem. 2002, 277:31994-32002.*
Patel et al., "A Novel Three Serum Phospholipid Panel Differentiates Normal Individuals from Those with Prostate Cancer," PLoS ONE 2014, 9(3):e88841.*
Welti et al., "Lipid species profiling: a high-throughput approach to identify lipid compositional changes and determine the function of genes involved in lipid metabolism and signaling," Curr. Opin. Plant Biol. 2004, 7:337-344.*

* cited by examiner

*Primary Examiner* — Kaijiang Zhang
(74) *Attorney, Agent, or Firm* — Thrive IP®; Jeremy M. Stipkala

(57) ABSTRACT

A method of diagnosing the presence of cancer in a subject without the need for a biopsy is provided. The method comprises obtaining a bio-sample from the subject and then extracting lipids from the bio-sample so as to form a serum of extracted lipids. Then the method includes combining a plurality of profiling substances to the serum of extracted lipids so as to form a profiling mixture. From the profiling mixture, the method identifies the amount and weight of a panel of biomarkers, wherein the panel of biomarkers comprise ePC 38:5, PC 40:3, and PC 42:4. Then said panel of biomarkers may be compared to a prediction ratio of the panel of biomarkers, whereby the comparison to the prediction ratio predicts the presence or absence of cancer in the subject.

7 Claims, No Drawings

BIOMARKER FOR HUMAN PROSTATE CANCER

CROSS-REFERENCE TO RELATED APPLICATION

This application claims the benefit of priority of U.S. provisional application No. 61/924,595, filed 7 Jan. 2014, the contents of which are herein incorporated by reference.

BACKGROUND OF THE INVENTION

The present invention relates to biomarkers associated with a cancer and, more particularly, to a panel of biomarkers and a method of using them to evaluate and identify early prostate cancer diagnosis and prognosis without the need for a biopsy.

Currently, there are no reliable biomarkers available to stratify abnormal or cancer versus normal individuals that do not involve a biopsy and histology exam by a specialist. Biopsies require the medical removal of tissue from a living subject in order to make the determination of the presence or extent of a disease; as a result, such procedures can be traumatic and fraught with many of the risks of having surgery. Other commonly used methods of evaluating prostate cancer involve the analysis of prostate specific antigen (PSA) and the use of digital rectal examination (DRE) screenings; however, such methods provide abstruse results leading to both under and over treatment of prostate cancer subjects.

As can be seen, there is an urgent need for a panel of biomarkers and a method of using them to evaluate and identify early cancer diagnosis and prognosis without the need for a biopsy.

SUMMARY OF THE INVENTION

In one aspect of the present invention, a method of diagnosing the presence of cancer in a subject without the need for a biopsy comprises: obtaining a bio-sample from the subject; extracting lipids from the bio-sample so as to form a serum of extracted lipids; combining a plurality of profiling substances to the serum of extracted lipids so as to form a profiling mixture; and identifying the amount and weight of a panel of biomarkers in the profiling mixture, wherein the panel of biomarkers comprise ePC 38:5, PC 40:3, and PC 42:4.

In another aspect of the present invention, a method of diagnosing the presence of prostate cancer in a subject without the need for a biopsy comprises: obtaining a bio-sample from the subject, wherein the bio-sample is blood, serum, or plasma; extracting lipids from the bio-sample so as to form a serum of extracted lipids; combining a plurality of profiling substances to the serum of extracted lipids so as to form a profiling mixture, wherein the plurality of profiling substances include di12:0-PC, di24:1-PC, 13:0-lysoPC, 19:0-lysoPC, di12:0-PE, di23:0-PE, 14:0-lysoPE, 18:0-lysoPE, 14:0-lysoPG, 18:0-lysoPG, di14:0-PA, di20:0(phytanoyl)-PA, di14:0-PS, di20:0(phytanoyl)-PS, 16:0-18:0-PI, di18:0-PI, C13:0 CE, and C23:0 CE; and wherein the profiling mixture is centrifuged for a suitable amount of time and at a suitable rate to pellet particulates; introducing unfractionated lipid extracts to the profiling mixture; using mass spectrometry to identify the amount and weight of a panel of biomarkers in the profiling mixture, wherein the panel of biomarkers comprise ePC 38:5, PC 40:3, and PC 42:4; and comparing the amount and weight of the panel of biomarkers to a prediction ratio, whereby the comparison to the prediction ratio predicts the presence or absence of cancer in the subject.

In yet another aspect of the present invention, a method of diagnosing the presence of cancer in a subject's bio-sample without the need for a biopsy, comprises: combining a plurality of profiling substances to the bio-sample so as to form a profiling mixture; and identifying the amount and weight of a panel of biomarkers in the profiling mixture, wherein the panel of biomarkers comprise ePC 38:5, PC 40:3, and PC 42:4.

These and other features, aspects and advantages of the present invention will become better understood with reference to the following drawings, description and claims.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, an embodiment of the present invention provides a method of diagnosing the presence of cancer in a subject without the need for a biopsy. The method comprises obtaining a bio-sample from the subject and then extracting lipids from the bio-sample so as to form a serum of extracted lipids. Then the method includes combining a plurality of profiling substances to the serum of extracted lipids so as to form a profiling mixture. From the profiling mixture, the method identifies the amount and weight of a panel of biomarkers, wherein the panel of biomarkers comprise ePC 38:5, PC 40:3, and PC 42:4. Then said panel of biomarkers may be compared to a prediction ratio of the panel of biomarkers, whereby the comparison to the prediction ratio predicts the presence or absence of cancer in the subject.

A biomarker generally refers to a measurable indicator of some biological state or condition; specifically, a biomarker indicates a change in expression or state of a protein that correlates with the risk or progression of a disease, or with the susceptibility of the disease to a given treatment. The present invention illustrates a panel of biomarkers embodied in a method for use in accurately predicting normal versus abnormal prostate cancer (PCa) in human subjects. The panel of biomarkers and related methods may involve the identification of sensitive and specific serum phospholipids, namely lipid species ePC 38:5, PC 40:3, and PC 42:4, forming a panel of specific biomarkers available to stratify cancer versus normal individuals especially without a need of biopsy. The sensitive or sensitivity refers to the proportion of individuals in a population that will be correctly identified when tested for a particular disease. The specific or specificity of a test refers to the probability that a person who does not have the particular disease and is tested for the disease will be correctly identified as not having the disease.

The method of using the present invention may include the following. First, a healthcare worker may obtain a predetermined bio-sample, such as blood and/or serum, from a subject. Then the lipid components found within the predetermined bio-serum may be statistically analyzed by any suitable sensitivity and specificity techniques for detecting prostate or disease abnormality. The statistical analysis may include but not be limited to cross-classifications and logistic regression modeling to screen the data for potential predictor candidates, false discovery rate adjustment for a large number of multiple comparisons, receiver operating characteristic curves for final models and cut-points determinations and assessments, and the like.

Then the method may include lipid extraction from the predetermined bio-sample by any suitable method, such as by using chloroform and methanol, to produce a serum of extracted lipids.

The method may further include lipid profiling on the extracted lipids. Lipid profiling may include forming a profiling mixture. The lipid profiling may include mass spectrometry, such as electro-spray ionization mass spectrometry. The profiling mixture may include a plurality of profiling batches of different components and various ratios thereof that form the profile mixture. By way of example, but not to be limited to, one profiling batch of the profiling mixture may be formed from an aliquot of 3 Ã,Â μl of the serum of extracted lipids combined with a plurality of profiling substances. In certain embodiments, the plurality of profiling substances may include 0.60 nmol di12:0-PC, 0.60 nmol di24:1-PC, 0.60 nmol 13:0-lysoPC, 0.60 nmol 19:0-lysoPC, 0.30 nmol di12:0-PE, 0.30 nmol di23:0-PE, 0.30 nmol 14:0-lysoPE, 0.30 nmol 18:0-lysoPE, 0.30 nmol 14:0-lysoPG, 0.30 nmol 18:0-lysoPG, 0.30 nmol di14:0-PA, 0.30 nmol di20:0 (phytanoyl)-PA, 0.20 nmol di14:0-PS, 0.20 nmol di20:0(phytanoyl)-PS, 0.23 nmol 16:0-18:0-PI, 0.16 nmol di18:0-PI, 2.5 nmol C13:0 CE, and 2.5 nmol C23:0 CE. In certain embodiments, the profiling mixture may be combined with solvents, such that the ratio of chloroform/methanol/300 mM ammonium acetate in water was 300/665/35, and the final volume was 1.2 ml.

Then the profiling mixture may be centrifuged for a suitable amount of time and at a suitable rate, typically 15 min at low speed, to pellet particulates. In certain embodiments, the unfractionated lipid extracts may be introduced to the profiling mixture by continuous infusion, by using an autosampler, or the like. In certain embodiments, the amount and type of lipids in the profiling mixture can be identified by other suitable techniques and processes.

The resulting profiling mixture may provide a consistency and robustness, facilitating identification of a plurality of specific serum phospholipids, wherein the plurality of specific serum phospholipids or panel of specific biomarkers fit certain criteria of a phase one/two biomarkers for PCa, especially if they can be combined with PSA and DRE screening for the diagnosis of PCa. For example, if the ePC 38:5 present in the profiling mixture of the predetermined bio-sample is greater than 0.015 nmoles, the PC 40:3 is less than 0.001 nmoles and the PC 42:4 is less than 0.0001 nmoles, then the predictability of the absence of PCa is 94%. Conversely, if the ePC 38:5 is less than 0.015 nmoles, the PC 40:3 is greater than 0.001 nmoles, and the PC 42:4 is greater than 0.0001 nmoles, then the predictability of the presence of PCa is very high. Therefore, a combination of ePC 38:5, PC 40:3 and PC 42:4 can be known as prediction ratio that may be used as a surrogate for the presence prostate cancer (PCa). The prediction ratio may be used to create tools to detect cancers and any disease states relevant to the lipid analyses.

It should be understood, of course, that the foregoing relates to exemplary embodiments of the invention and that modifications may be made without departing from the spirit and scope of the invention as set forth in the following claims.

What is claimed is:

1. A method of detecting ePC 38:5, PC 40:3, and PC 42:4 in a subject, comprising:
    obtaining a bio-sample from the subject without biopsy, the bio-sample being blood, serum, or plasma;
    extracting lipids from the bio-sample so as to form a composition of extracted lipids;
    combining a plurality of profiling substances to the composition of extracted lipids so as to form a profiling mixture; and
    identifying the amount of ePC 38:5, PC 40:3, and PC 42:4 in the profiling mixture, thereby detecting the ePC 38:5, PC 40:3, and PC 42:4 in the subject.

2. The method of claim 1, further including comparing the amount of the ePC 38:5, PC 40:3, and PC 42:4 to a prediction ratio,
    whereby the comparison to the prediction ratio predicts the presence or absence of prostate cancer in the subject.

3. The method of claim 1, wherein the plurality of profiling substances include at least one of di12:0-PC, di24:1-PC, 13:0-lysoPC, 19:0-lysoPC, di12:0-PE, di23:0-PE, 14:0-lysoPE, 18:0-lysoPE, 14:0-lysoPG, 18:0-lysoPG, di14:0-PA, di20:0 (phytanoyl)-PA, di14:0-PS, di20:0 (phytanoyl)-PS, 16:0-18:0-PI, di18:0-PI, C13:0 CE, and C23:0 CE.

4. The method of claim 1, wherein identifying the amount of the ePC 38:5, PC 40:3, and PC 42:4 involves using mass spectrometry.

5. The method of claim 1, wherein the profiling mixture is centrifuged for a suitable amount of time and at a suitable rate to pellet particulates.

6. The method of claim 5, further including introducing unfractionated lipid extracts to the profiling mixture.

7. A method of diagnosing the presence of prostate cancer in a subject, comprising:
    obtaining a bio-sample without biopsy from the subject, wherein the bio-sample is blood, serum, or plasma;
    extracting lipids from the bio-sample so as to form a composition of extracted lipids;
    combining a plurality of profiling substances to the composition of extracted lipids so as to form a profiling mixture, wherein the plurality of profiling substances include at least one of di12:0-PC, di24:1-PC, 13:0-lysoPC, 19:0-lysoPC, di12:0-PE, di23:0-PE, 14:0-lysoPE, 18:0-lysoPE, 14:0-lysoPG, 18:0-lysoPG, di14:0-PA, di20:0 (phytanoyl)-PA, di14:0-PS, di20:0 (phytanoyl)-PS, 16:0-18:0-PI, di18:0-PI, C13:0 CE, and C23:0 CE; and wherein the profiling mixture is centrifuged for a suitable amount of time and at a suitable rate to pellet particulates;
    introducing unfractionated lipid extracts to the profiling mixture;
    using mass spectrometry to identify the amount of ePC 38:5, PC 40:3, and PC 42:4 in the profiling mixture; and
    diagnosing the presence of prostate cancer in the subject when the amount of ePC 38:5 is less than 0.015 nmoles, the amount of PC 40:3 is greater than 0.001 nmoles, and the amount of PC 42:4 is greater than 0.0001 nmoles.

* * * * *